US005635348A

United States Patent [19]

Leong

[11] Patent Number: 5,635,348
[45] Date of Patent: Jun. 3, 1997

[54] METHOD AND PROBES FOR IDENTIFYING BACTERIA FOUND IN BLOOD

[75] Inventor: Diane U. Leong, Berkeley, Calif.

[73] Assignee: Hoffmann-La Roche Inc., Nutley, N.J.

[21] Appl. No.: 348,683

[22] Filed: Dec. 2, 1994

Related U.S. Application Data

[63] Continuation of Ser. No. 973,334, Nov. 6, 1992, abandoned, which is a continuation-in-part of Ser. No. 696,448, May 6, 1991, abandoned, which is a continuation-in-part of Ser. No. 593,176, Oct. 5, 1990, abandoned.

[51] Int. Cl.$^6$ ............................................. C12Q 1/68
[52] U.S. Cl. ........................ 435/6; 536/23.1; 536/24.32
[58] Field of Search .................... 435/6, 91.2; 536/23.1, 536/24.32

[56] References Cited

U.S. PATENT DOCUMENTS

| | | | |
|---|---|---|---|
| 4,683,195 | 7/1987 | Mullis et al. | 435/91 |
| 4,683,202 | 7/1987 | Mullis | 435/91 |
| 4,717,653 | 1/1988 | Webster | 435/5 |
| 4,800,159 | 1/1989 | Mullis et al. | 435/91 |
| 4,820,630 | 4/1989 | Taub | 435/5 |
| 4,851,330 | 7/1989 | Kohne | 435/6 |
| 4,977,251 | 12/1990 | Salyers et al. | 536/24.32 |
| 5,084,565 | 1/1992 | Parodos et al. | 536/27 |
| 5,232,829 | 8/1993 | Longiaru et al. | 435/6 |

FOREIGN PATENT DOCUMENTS

| | | |
|---|---|---|
| 0 314 294 | 9/1988 | European Pat. Off. . |
| 88/03957 | 6/1988 | WIPO . |
| 90/11370 | 10/1990 | WIPO . |
| WO 90/15157 | 12/1990 | WIPO . |

OTHER PUBLICATIONS

Neefs et al., Nuc. Acids Res., 18:2237–2317 (1990).
Weisburg et al., J. Bacteriol., 164:230–236 (1985).
Carbon et al., FEBS Letters, 94:152–156 (1978).
Wilson et al., J. Clin. Micro., 28:1942–1946 (Sep. 1990).
Bottger, E.C., FEMS Micro. Ltrs., 65:171–176 (1989).
Woese, et al., Science, 229:762–765 (1985).
Tsuru et al., Chem. Abst., 110:111361c (1989).
Stackebrandt et al., Intl. J. System. Bacteriology, 38:354–357 (.
Pramanik et al., Arch. Biochem. & Biophysics, 235:276–282 (1984).
Tsuru et al., Med. Immunology, 16:827–833 (1988).
Lane et al., PNAS, 82:6955–6959 (1985).
White et al., in PCR Protocols: A Guide to Methods and Applications, 315–322 (1990).
Medlin et al., Gene, 71:491–499 (1988).
Atlas and Bej, in PCR Protocols: A Guide to Methods and Applications, 399–406 (1990).
Olive, Michael D., Clin. Micro. 27:261–265 (1989).
Wood et al., PNAS, 82:1585–1588 (1985).
Woese, Carl R., Micro. Reviews, 51:221–271 (1987).
Bryan, Charles S., Clin. Micro. Reviews, 2:329–353 (1989).
Kocher and White, Chap. 13 of PCR Technology: Principles and Applications for DNA Amplification, pp. 137–147 (1989).
Barry et al., Biotechnology, 8:233–236 (1990).
Kocher et al., PNAS, 86:6196–6200 (1989).
"Compilation of Small Ribosomal Subunit RNA Sequences" Nucleic Acids Research, vol. 19, pp. 1985–2003, (Supplement—1991).

*Primary Examiner*—Scott W. Houtteman
*Attorney, Agent, or Firm*—George W. Johnston; Patricia S. Rocha-Tramaloni; Raina Semionow

[57] ABSTRACT

Methods and reagents are provided for detecting polynucleotide sequences in bacteria using probes specific for gram-negative and gram-positive bacteria and other specific bacterial species or groups of species respectively. Also provided are methods of amplification using primers specific for bacterial species.

5 Claims, 7 Drawing Sheets

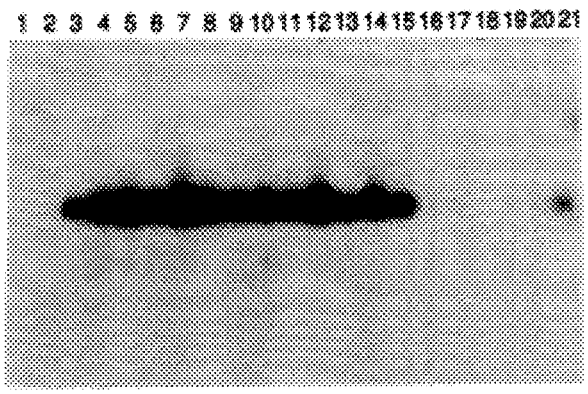
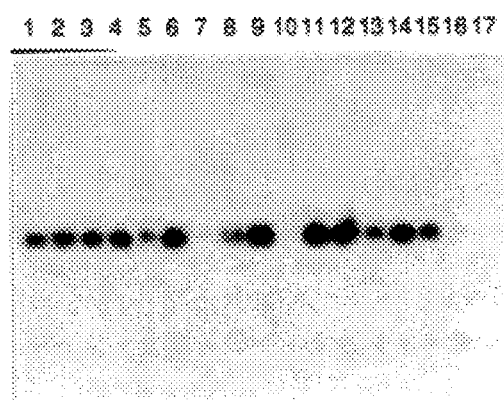

1. Thermotoga maritima
2. Thermus thermophilus
3. Shigella boydii
4. S. dysenteriae
5. S. flexneri
6. S. sonnei
7. Enterobacter aerogenes
8. Klebsiella pneumoniae
9. Salmonella typhimurium
10. Serratia marcescens
11. Pseudomonas aeruginosa
12. Treponema vincentii
13. Thermus aquaticus
14. Acetobacter sp.
15. Acetobacter sp.
16. Staphylococcus aureus
17. Clostridium perfringens
18. Micrococcus lysodeikticus
19. Bacillus subtilis
20. B. amyloliquefaciens
21. Streptomyces hygroscopicus 1. Enterobacter aerogenes
2. Klebsiella pneumoniae
3. Salmonella typhimurium
4. Serratia marcescens
5. Pseudomonas aeruginosa
6. Treponema vincentii
7. Thermus aquaticus
8. Staphylococcus aureus
9. Clostridium perfringens
10. Micrococcus lysodeikticus
11. Bacillus subtilis
12. B. amyloliquefaciens
13. Streptomyces hygroscopicus
14. Acetobacter sp.
15. Acetobacter sp.
16. Escherichia coli
17. no DNA

FIG. 1

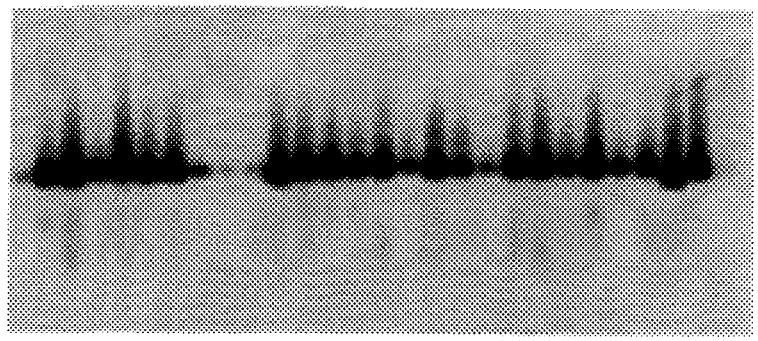
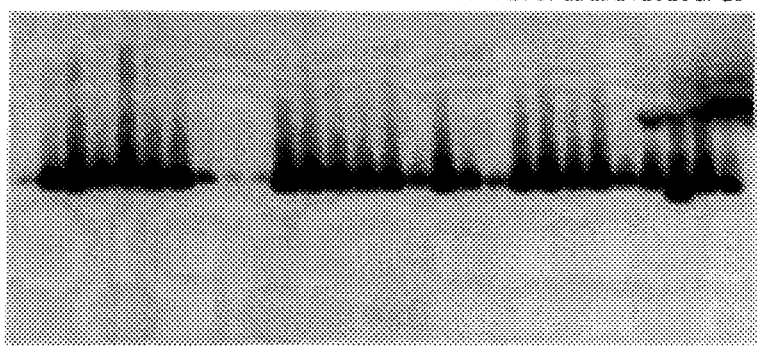
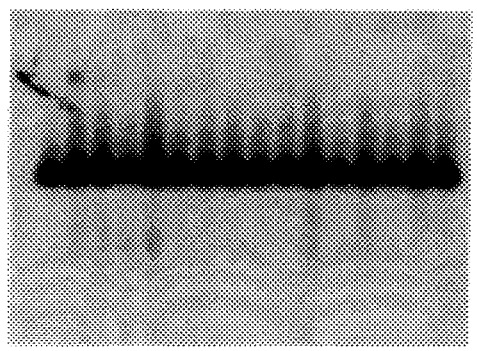
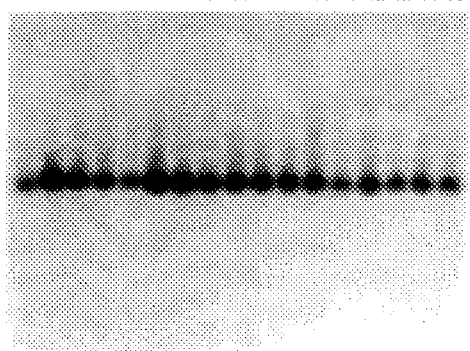
FIG. 2

| HYBRIDIZATION RESULTS | Gram Positive/ | Probes | |
|---|---|---|---|
| STRAIN | Gram Negative | DL04 | RW04 |
| Thermotoga maritima | Neither | - | N.D. |
| Thermus thermophilus | Neither | - | N.D. |
| Shigella boydii | - | + | N.D. |
| S. dysenteriae | - | + | N.D. |
| S. flexneri | - | + | N.D. |
| S. sonnei | - | + | N.D. |
| Enterobacter aerogenes | - | + | + |
| Klebsiella pneumoniae | - | + | + |
| Salmonella typhimurium | - | + | + |
| Serratia marcescens | - | + | + |
| Pseudomonas aeruginosa | - | + | + |
| Treponema vincentii | Neither | + | + |
| Thermus aquaticus | Neither | + | - |
| Acetobacter sp. | - | + | + |
| Acetobacter sp. | - | + | + |
| Staphylococcus aureus | + | - | + |
| Clostridium perfringens | + | - | + |
| Micrococcus lysodeikticus | + | - | - |
| Bacillus subtilis | + | - | + |
| B. amyloliquefaciens | + | - | + |
| Streptomyces hygroscopicus | + | + | + |
| N.D. indicates not done | | | |

| STRAIN | REFERENCE | Gram-<br>DL04 | Gram-<br>RDR278 | Bacteroides<br>RDR279 | universal<br>RDR244 | universal<br>RDR245 |
|---|---|---|---|---|---|---|
| GRAM-POSITIVE | | | | | | |
| Actinomyces israelii | ATCC 12102 | +/− | - | - | + | + |
| Aerococcus viridans | ATCC 11563 | - | - | - | + | + |
| Bacillus amyloliquefaciens | H | - | N.D. | N.D. | N.D. | N.D. |
| Bacillus subtilis | ATCC 6051 | - | - | - | + | + |
| B. subtilis | | - | N.D. | N.D. | N.D. | N.D. |
| Bifidobacterium adolescentis | ATCC 15703 | - | - | - | + | + |
| Brevibacterium linens | ATCC 9172 | - | - | - | + | + |
| Clostridium innocuum | ATCC 14501 | - | - | - | + | + |
| C. perfringens | ATCC 13124 | - | - | - | + | + |
| C. perfringens | Sigma | - | N.D. | N.D. | N.D. | N.D. |
| Corynebacterium genitalium | ATCC 33030 | +/− | - | - | + | + |
| C. pseudotuberculosis | ATCC 19410 | - | - | - | + | + |
| C. xerosis | ATCC 373 | +/− | - | - | + | + |
| Deinococcus radiopugnans | ATCC 19172 | - | - | - | + | + |
| Enterococcus avium | ATCC 14025 | - | - | - | + | + |
| E. faecalis | ATCC 19433 | - | - | - | + | + |
| E. faecium | ATCC 19434 | - | - | - | + | + |
| Erysipelothrix rhusiopathiae | ATCC 19414 | - | - | - | + | + |
| Gardnerella vaginalis | ATCC 14018 | - | - | - | + | + |
| Gemella haemolysans | ATCC 10379 | +/− | - | - | + | + |
| Lactobacillus acidophilus | ATCC 4356 | - | - | - | + | + |
| L. brevis | ATCC 14869 | - | - | - | + | + |
| L. jensenii | ATCC 25258 | - | - | - | + | + |
| Lactococcus lactis cremoris | ATCC 19257 | - | - | - | + | + |
| L. lactis lactis | ATCC 19435 | - | - | - | + | + |
| Leuconostoc paramesenteroides | ATCC 33313 | - | - | - | + | + |
| Listeria monocytogenes | ATCC 15313 | - | - | - | + | + |
| Micrococcus luteus | ATCC 4698 | N.D. | - | - | + | + |
| M. lysodeikticus | Sigma | - | N.D. | N.D. | N.D. | N.D. |
| Mycobacterium bovis | | - | N.D. | N.D. | N.D. | N.D. |

| STRAIN | REFERENCE | Gram-<br>DL04 | Gram-<br>RDR278 | Bacteroides<br>RDR279 | universal<br>RDR244 | universal<br>RDR245 |
|---|---|---|---|---|---|---|
| GRAM-POSITIVE | | | | | | |
| M. gordonae | ATCC 14470 | + | - | - | + | + |
| M. smegmatis | ATCC 19420 | + | - | - | + | + |
| M. tuberculosis | | - | N.D. | N.D. | N.D. | N.D. |
| Mycoplasma genitalium | ATCC 33530 | + | - | - | + | + |
| M. hominis | ATCC 23114 | - | - | - | + | + |
| M. pneumoniae | ATCC 15531 | - | - | - | + | + |
| Pediococcus acidilactici | ATCC 33314 | - | - | - | + | + |
| Peptostreptococcus anaerobius | ATCC 27337 | - | - | - | - | + |
| P. magnus | ATCC 15794 | ± | - | - | + | + |
| Propionibacterium acnes | ATCC 6919 | - | - | - | + | + |
| Staphylococcus aureus | ATCC 12598 | - | - | - | + | + |
| S. aureus | ATCC 33589 | - | N.D. | N.D. | N.D. | N.D. |
| S. aureus | ATCC 25923 | - | N.D. | N.D. | N.D. | N.D. |
| S. epidermidis | ATCC 14990 | - | - | - | + | + |
| Streptococcus agalactiae | ATCC 13813 | - | - | - | + | + |
| S. bovis | ATCC 33317 | - | - | - | + | + |
| S. dysgalactiae | ATCC 43078 | - | N.D. | N.D. | N.D. | N.D. |
| S. equinus | ATCC 9812 | - | - | - | + | + |
| S. intermedius | ATCC 27335 | - | - | - | + | + |
| S. mitis | ATCC 33399 | - | - | - | + | + |
| S. mutans | ATCC 25175 | - | - | - | + | + |
| S. pneumoniae | ATCC 33400 | - | - | - | + | + |
| S. pyogenes | ATCC 12344 | - | - | - | + | + |
| S. pyogenes | ATCC 12344 | ± | N.D. | N.D. | N.D. | N.D. |
| S. salivarius | ATCC 13419 | ± | - | - | + | + |
| S. sanguis | ATCC 10556 | - | - | - | + | + |
| S. uberis | ATCC 19436 | - | - | - | + | + |
| Streptomyces griseinus | ATCC 23915 | | | | | |
| S. hygroscopicus | 21705 | - | N.D. | N.D. | N.D. | N.D. |
| Ureaplasma urealyticum | ATCC 27618 | + | - | - | + | + |

| STRAIN | REFERENCE | Gram- DL04 | Gram- RDR278 | Bacteroides RDR279 | Universal RDR244 | Universal RDR245 |
|---|---|---|---|---|---|---|
| GRAM-NEGATIVE | | | | | | |
| Acinetobacter calcoaceticus | ATCC 23055 | + | ± | - | + | + |
| Acinetobacter lwoffi | ATCC 15309 | + | ± | - | + | + |
| Achromobacter xerosis | ATCC 14780 | + | ± | - | + | + |
| Aeromonas hydrophila | ATCC 7966 | + | + | - | + | + |
| Agrobacterium radiobacter | ATCC 19358 | ± | + | - | + | ± |
| Alcaligenes denitrificans | ATCC 27061 | - | + | - | + | + |
| A. faecalis | ATCC 8750 | - | + | - | + | + |
| Bacteroides fragilis | ATCC 25285 | - | - | + | + | + |
| Branhamella catarrhalis | ATCC 25238 | + | ± | - | + | + |
| Campylobacter fetus | ATCC 27374 | + | + | - | + | + |
| C. jejuni | ATCC 33560 | + | + | - | + | + |
| Chromobacterium violaceum | ATCC 12472 | - | + | - | + | + |
| Citrobacter freundii | ATCC 8090 | + | ± | - | + | + |
| Derxia gummosa | ATCC 15994 | - | + | - | + | + |
| Edwardsiella tarda | ATCC15947 | + | ± | - | + | + |
| Eikenella corrodens | ATCC 23834 | - | + | - | + | + |
| Enterobacter aerogenes | ATCC 13048 | + | N.D. | N.D. | N.D. | N.D. |
| Enterobacter cloacae | ATCC 13047 | + | ± | - | + | + |
| Escherichia coli | ATCC 11775 | + | + | - | + | + |
| Flavobacterium meningosepticum | ATCC 13253 | N.D. | N.D. | N.D. | N.D. | N.D. |
| Haemophilus ducreyi | ATCC 33940 | + | ± | - | + | + |
| Haemophilus influenzae | ATCC 33391 | - | - | - | + | + |
| H. influenzae | ATCC 33391 | + | N.D. | N.D. | N.D. | N.D. |
| Kingella kingae | ATCC 23330 | + | ± | - | + | + |
| Klebsiella pneumoniae | ATCC 13883 | - | - | - | + | + |
| K. pneumoniae | CMCC 151 | + | N.D. | N.D. | N.D. | N.D. |
| Legionella bozemanii | ATCC 33217 | + | ± | - | + | + |
| Legionella pneumophila | ATCC 33152 | + | + | - | + | + |
| Moraxella osloensis | ATCC 19976 | + | ± | - | + | + |
| Morganella morganii | ATCC 25830 | - | N.D. | N.D. | N.D. | N.D. |

| STRAIN | REFERENCE | Gram- DL04 | Gram- RDR278 | Bacteroides RDR279 | Universal RDR244 | Universal RDR245 |
|---|---|---|---|---|---|---|
| GRAM-NEGATIVE | | | | | | |
| Neisseria gonorrhoeae | ATCC 19424 | - | + | - | + | + |
| N. gonorrhoeae | CMCC 2783 | N.D. | N.D. | N.D. | N.D. | N.D. |
| N. meningitidis | ATCC 13077 | - | + | - | + | + |
| N. meningitidis | CMCC 2801 | N.D. | N.D. | N.D. | N.D. | N.D. |
| Paracoccus denitrificans | ATCC 17741 | + | + | - | + | + |
| Proteus mirabilis | ATCC 29906 | + | +/- | - | + | + |
| Providencia stuartii | ATCC 29914 | + | +/- | - | + | + |
| Pseudomonas aeruginosa | ATCC 10145 | + | +/- | - | + | + |
| P. aeruginosa | ATCC 27853 | + | N.D. | N.D. | N.D. | N.D. |
| Pseudomonas putida | ATCC 12633 | + | +/- | - | + | + |
| Rahnella aquatilis | ATCC 33071 | + | +/- | - | + | + |
| Rhodospirillum rubrum | ATCC 11170 | - | +/- | - | + | + |
| Salmonella typhimurium | CMCC 2 | + | N.D. | N.D. | N.D. | N.D. |
| Serratia marcescens | ATCC 13880 | + | N.D. | N.D. | N.D. | N.D. |
| S. marcescens | CMCC 186 | + | N.D. | N.D. | N.D. | N.D. |
| Shigella boydii | | + | N.D. | N.D. | N.D. | N.D. |
| S. dysenteriae | | + | N.D. | N.D. | N.D. | N.D. |
| S. flexneri | | + | N.D. | N.D. | N.D. | N.D. |
| S. sonnei | | + | N.D. | N.D. | N.D. | N.D. |
| Vibrio parahaemolyticus | ATCC 17802 | N.D. | N.D. | N.D. | N.D. | N.D. |
| Yersinia enterocolitica | ATCC 9610 | + | +/- | - | + | + |

FIG. 4-4

SEQUENCE LISTING ( 1 ) GENERAL INFORMATION:

( i i i ) NUMBER OF SEQUENCES: 25

( 2 ) INFORMATION FOR SEQ ID NO:1:

( i ) SEQUENCE CHARACTERISTICS:
  ( A ) LENGTH: 19 base pairs
  ( B ) TYPE: nucleic acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO:1:

AGGAGGTGAT CCAACCGCA                                                  19

( 2 ) INFORMATION FOR SEQ ID NO:2:

( i ) SEQUENCE CHARACTERISTICS:
  ( A ) LENGTH: 20 base pairs
  ( B ) TYPE: nucleic acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO:2:

AACTGGAGGA AGGTGGGGAT                                                 20

( 2 ) INFORMATION FOR SEQ ID NO:3:

( i ) SEQUENCE CHARACTERISTICS:
  ( A ) LENGTH: 28 base pairs
  ( B ) TYPE: nucleic acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO:3:

GACGTCAAAT CATCATGCCC CTTATGTC                                        28

( 2 ) INFORMATION FOR SEQ ID NO:4:

( i ) SEQUENCE CHARACTERISTICS:
  ( A ) LENGTH: 28 base pairs
  ( B ) TYPE: nucleic acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO:4:

GACGTCAAGT CATCATGGCC CTTACGTC       28

( 2 ) INFORMATION FOR SEQ ID NO:5:

( i ) SEQUENCE CHARACTERISTICS:
  ( A ) LENGTH: 28 base pairs
  ( B ) TYPE: nucleic acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO:5:

GACGTAAGGG CCATGATGAC TTGACGTC       28

( 2 ) INFORMATION FOR SEQ ID NO:6:

( i ) SEQUENCE CHARACTERISTICS:
  ( A ) LENGTH: 22 base pairs
  ( B ) TYPE: nucleic acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO:6:

GTAAGGGCCA TGATGACTTG AC       22

( 2 ) INFORMATION FOR SEQ ID NO:7:

( i ) SEQUENCE CHARACTERISTICS:
  ( A ) LENGTH: 28 base pairs
  ( B ) TYPE: nucleic acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO:7:

GACGTAAGGG CCATGAGGAC TTGACGTC       28

( 2 ) INFORMATION FOR SEQ ID NO:8:

( i ) SEQUENCE CHARACTERISTICS:
  ( A ) LENGTH: 27 base pairs
  ( B ) TYPE: nucleic acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO:8:

CGGTGAATAC GTTCCCGGGC CTTGTAC       27

( 2 ) INFORMATION FOR SEQ ID NO:9:

( i ) SEQUENCE CHARACTERISTICS:
  ( A ) LENGTH: 27 base pairs
  ( B ) TYPE: nucleic acid
  ( C ) STRANDEDNESS: single

```
            ( D ) TOPOLOGY: linear ( i i ) MOLECULE TYPE: DNA (genomic)

( x i ) SEQUENCE DESCRIPTION: SEQ ID NO:9:

GTACAAGGCC  CGGGAACGTA  TTCACCG                                                    27

( 2 ) INFORMATION FOR SEQ ID NO:10:

( i ) SEQUENCE CHARACTERISTICS:
                ( A ) LENGTH: 25 base pairs
                ( B ) TYPE: nucleic acid
                ( C ) STRANDEDNESS: single
                ( D ) TOPOLOGY: linear ( i i ) MOLECULE TYPE: DNA (genomic)

( x i ) SEQUENCE DESCRIPTION: SEQ ID NO:10:

GGCGCTTACC  ACTTTGTGAT  TCATG                                                      25

( 2 ) INFORMATION FOR SEQ ID NO:11:

( i ) SEQUENCE CHARACTERISTICS:
                ( A ) LENGTH: 28 base pairs
                ( B ) TYPE: nucleic acid
                ( C ) STRANDEDNESS: single
                ( D ) TOPOLOGY: linear ( i i ) MOLECULE TYPE: DNA (genomic)

( x i ) SEQUENCE DESCRIPTION: SEQ ID NO:11:

GACGTAAGGG  CCGTGCTGAT  TTGACGTC                                                   28

( 2 ) INFORMATION FOR SEQ ID NO:12:

( i ) SEQUENCE CHARACTERISTICS:
                ( A ) LENGTH: 28 base pairs
                ( B ) TYPE: nucleic acid
                ( C ) STRANDEDNESS: single
                ( D ) TOPOLOGY: linear ( i i ) MOLECULE TYPE: DNA (genomic)

( x i ) SEQUENCE DESCRIPTION: SEQ ID NO:12:

GACCTAAGGG  CCATGATGAC  TTGACGTC                                                   28

( 2 ) INFORMATION FOR SEQ ID NO:13:

( i ) SEQUENCE CHARACTERISTICS:
                ( A ) LENGTH: 28 base pairs
                ( B ) TYPE: nucleic acid
                ( C ) STRANDEDNESS: single
                ( D ) TOPOLOGY: linear ( i i ) MOLECULE TYPE: DNA (genomic)

( x i ) SEQUENCE DESCRIPTION: SEQ ID NO:13:

GACATAAGGG  CCATGAGGAC  TTGACGTC                                                   28

( 2 ) INFORMATION FOR SEQ ID NO:14:

( i ) SEQUENCE CHARACTERISTICS:
                ( A ) LENGTH: 25 base pairs
                ( B ) TYPE: nucleic acid
                ( C ) STRANDEDNESS: single
                ( D ) TOPOLOGY: linear ( i i ) MOLECULE TYPE: DNA (genomic)

( x i ) SEQUENCE DESCRIPTION: SEQ ID NO:14:
```

GAGACCGGCT TTCCGAGATT CGCTC 25

( 2 ) INFORMATION FOR SEQ ID NO:15:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:15:

CCAACTTTCA TGACTTGACG GG 22

( 2 ) INFORMATION FOR SEQ ID NO:16:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:16:

AGTAACCATT TGGAGCTAGC CGT 23

( 2 ) INFORMATION FOR SEQ ID NO:17:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:17:

CGGCTAGCTC TAAAAGGTTA CTCTA 25

( 2 ) INFORMATION FOR SEQ ID NO:18:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:18:

CGGCTAGCTC CAAAAGGTTA CTCTA 25

( 2 ) INFORMATION FOR SEQ ID NO:19:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:19:

CGACGGCTAG CTCCAAATGG TTACT 25

( 2 ) INFORMATION FOR SEQ ID NO:20:

( i ) SEQUENCE CHARACTERISTICS:
    ( A ) LENGTH: 25 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:20:

CACATGCTAC AAGGGTCGGT ACAGT 25

( 2 ) INFORMATION FOR SEQ ID NO:21:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:21:

ACTGTACCGA CCATTGTAGC ATGTG 25

( 2 ) INFORMATION FOR SEQ ID NO:22:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:22:

GTATTCACCG CGGCATGCTG ATCCG 25

( 2 ) INFORMATION FOR SEQ ID NO:23:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:23:

TATTCACCGC GGCATGCTGA T 21

( 2 ) INFORMATION FOR SEQ ID NO:24:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:24:

GCCGGTGGAG TAACCTTTTA GGAGC 25

( 2 ) INFORMATION FOR SEQ ID NO:25:

( i ) SEQUENCE CHARACTERISTICS:
        ( A ) LENGTH: 22 base pairs
        ( B ) TYPE: nucleic acid
        ( C ) STRANDEDNESS: single (D) TOPOLOGY: linear (ii) MOLECULE TYPE: DNA (genomic)

(xi) SEQUENCE DESCRIPTION: SEQ ID NO:25:

CCGGTGGAGT AACCTTTTAG GA     22

METHOD AND PROBES FOR IDENTIFYING BACTERIA FOUND IN BLOOD

This is a continuation of application Ser. No. 07/973,334 filed Nov. 6, 1992, abandoned, which is a continuation-in-part of Ser. No. 07/696,448, filed Mar. 6, 1991, now abandoned, which is a continuation-in-part of Ser. No. 07/593,176, filed Oct. 5, 1990, now abandoned.

TECHNICAL FIELD

The present invention relates generally to methods and reagents for identifying and detecting gram-positive, gram-negative bacteria and other bacteria found in human blood samples.

BACKGROUND OF THE INVENTION

In order to successfully treat a disease caused by a bacterium the rapid and accurate detection and identification of the disease-causing bacterium is required. Bacterial detection and identification have traditionally been accomplished by pure culture isolation, followed by identification procedures that make use of knowledge of specimen source, growth requirements, visible (colony) growth features, microscopic morphology, staining reactions, and biochemical characteristics.

An important step in determining the identity of a bacterium is the Gram stain. This procedure involves treating a heat-fixed bacterial smear on a glass slide with the basic dye, crystal violet. All organisms take up the dye. The smear is then covered with Greta's iodine solution (3 percent iodine-potassium iodide in water or a weak buffer, pH 8.0, in order to neutralize acidity formed from iodine on standing). After a water rinse and decolofization with acetone, the preparation is washed thoroughly in water and counterstained with a red dye, usually safranin. The stained preparation is then rinsed with water, dried, and examined under oil using a light microscope.

Most bacteria can be differentiated into two groups by this stain. Gram-positive organisms stain blue, whereas about one-third of the cocci, one-half of the bacilli, and all spiral organisms stain red and are said to be gram-negative. This method, while effective, is very time consuming and involves many different procedures which present many opportunities for error. For blood samples the Gram stain and other culture-based methods of detection require incubation of the sample with culture medium at least overnight in order to obtain a pure culture.

The presence of bacteria or fungi in the blood, commonly referred to as septicemia, can have severe and life-threatening clinical consequences. Septicernie can result in septic shock, which includes the following symptoms—hypotension, lactic acidosis, hypoxemia, oligouria, confusion, disseminated intravascular coagulation, gastrointestinal bleeding, disturbances of metabolism, and subtle skin lesions. As little as one colony-forming unit (CFU) may be present in a 30 ml blood sample in a patient with septicemia. Since culture is currently the most sensitive and commonly used method of detecting bacteria or fungi in the blood, treatment of suspected septicemia is often begun empirically, without waiting for the results of culture. It is clear that a rapid diagnostic method for detecting bacteria in the blood with the same sensitivity as culture would be a significant improvement over currently used methods.

SUMMARY OF THE INVENTION

The present invention pertains to methods and reagents for the rapid detection and identification of bacteria causing septicemia. The detection is based upon the hybridization of nucleotide probes to nucleotide sequences as well as transcripts therefrom present in defined species or groups of species but not in others.

In a preferred embodiment, a target region from genomic DNA or from a reverse transcript of 16S rRNA is amplified and the resultant amplified DNA is treated with a panel of probes which can hybridize to the DNA of a species or group of species of bacteria but not to others. The probes which successfully hybridize to the amplified DNA are determined and the bacterium is classified as either gram-positive or gram-negative or as a particular species or group of species depending on which probes hybridize to the amplified DNA.

Also defined and claimed herein are specific probes and their complements for identifying gram-negative and gram-positive and other bacteria causing septicemia.

The invention further contemplates the formulation and use of Polymerase Chain Reaction (PCR) kits containing universal bacterial primers for amplifying a specific universal target region of DNA for all bacteria and a panel of probes which hybridize to a nucleotide sequence which is unique to a species or group of species of bacteria within that target region.

BRIEF DESCRIPTION OF THE DRAWING

FIG. 1 shows a photograph of an autoradiograph of Southern blots hybridized with candidate Gram-negative probes RW04 (SEQ ID No. 4) and DL04 (SEQ ID No. 5).

FIG. 2 shows a photograph of autoradiographs of Southern blots hybridized with candidate universal bacterial probes RDR244 (SEQ ID No. 8) and RDR245 (SEQ ID No. 9).

FIG. 3 summarizes the hybridization data on gram-negative probes RW04 (SEQ ID No. 4) and DL04 (SEQ ID No. 4) shown in FIG. 1.

FIG. 4 summarizes the results of testing probes RDR278 (SEQ ID No. 7) and DL04 (SEQ ID No. 5), the gram-negative probes; RDR244 (SEQ ID No. 8) and RDR245 (SEQ ID No. 9), two candidate universal bacterial probes; and RDR279 (SEQ ID No. 11), the Bacteroides probe.

DETAILED DESCRIPTION OF THE INVENTION

The present invention is a method for determining the presence of and identification of bacteria by means of hybridizing probes to nucleotide sequences which are unique to either gram-positive or gram-negative bacteria or to a species or group of species of bacteria.

The use of specific polynucleotide sequences as probes for the recognition of infectious agents is becoming a valuable alternative to problematic immunological identification assays. For example, PCT publication W084/02721, published Jul. 19, 1984 describes the use of nucleic acid probes complementary to targeted nucleic acid sequences composed of ribosomal RNA, transfer RNA, or other RNA in hybridization procedures to detect the target nucleic acid sequence. While the assay may provide greater sensitivity and specificity than known DNA hybridization assays, hybridization procedures which require the use of a complementary probe are generally dependent upon the cultivation of a test organism and are, therefore, unsuitable for rapid diagnosis. Probes can be used directly on clinical specimens if a means of amplifying the DNA target is available.

For use in the present invention, probes for bacterial species or groups of species causing septicemia include but are not limited to:

universal bacterial probe
Gram-negative probes
Gram-positive probe
*Escherichia coli*/enteric bacteria probe
Bacteroides probe These probes are useful in hybridizing to DNA or RNA amplified by the Polymerase Chain Reaction (PCR). Probes for detecting *E. coli*/enteric bacteria are also suitable for detecting bacteria indicative of meningitis in cerebrospinal fluid (see copending PCT/US92/06365, filed Jul. 31, 1992, which is incorporated herein by reference). Also contemplated herein is a panel of probes which will allow the detection and identification of bacteria commonly found in blood. The panel includes probes for the bacteria causing septicemia listed above as well as bacterial species which are commonly considered contaminants of human blood. Such contaminant species are also capable of causing septicemia; however, these organisms do so at a lower frequency than the agents listed above and include: Bacillus species, Corynebacterium species, Propionibacterium species, *Staphylococcus epidermidis*, Saureus, and other coagulase-negative Staphylococci (*Bergey's Manual of Systematic Bacteriology*, ed. J. G. Holt, Williams and Wilkins, Baltimore, MD, which is incorporated herein by reference). Suitable probes for detecting these contaminating species are also described in PCT/US92/06365.

PCR is a powerful nucleic acid amplification technique that can be used for the detection of small numbers of pathogens whose in vitro cultivation is difficult or lengthy, or as a substitute for other methods which require the presence of living specimens for detection. In its simplest form, PCR is an in vitro method for the enzymatic synthesis of specific DNA sequences, using two oligonucleotide primers that hybridize to opposite strands and flank the region of interest in the target DNA. A repetitive series of cycles involving template denaturation, primer annealing, and the extension of the annealed primers by DNA polymerase results in the exponential accumulation of a specific fragment whose termini are defined by the 5' ends of the palmers. PCR reportedly is capable of producing a selective enrichment of a specific DNA sequence by a factor of $10^{12}$. The PCR method is described in Saiki et.al., 1985, *Science* 230:1350 and is the subject of U.S. Pat. Nos. 4,683,195, 4,683,202 and 4,800,159 (these references are incorporated herein by reference). This method has been used to detect the presence of the aberrant sequence in the beta-globin gene which is related to sickle cell anemia (Saiki et al., 1985, supra) and the human immunodeficiency virus (HIV) RNA (Byrne et al., 1988, *Nuc. Acids Res.* 16:4165).

The invention provides methods for determining the presence of a bacterial polynucleotide in samples suspected of containing said polynucleotide, wherein said polynucleotide contains a selected target region, said method comprising:

(a) amplifying the target region, if any, to a detectable level;

(b) providing a polynucleotide probe or probes containing a sequence which is complementary to a polynucleotide sequence characteristic of the bacterial species or group of species or a subset of said unique sequence in the target region;

(c) incubating the amplified target region, if any, with the polynucleotide probe or probes under conditions which allow specificity of hybrid duplexes; and (d) detecting hybrids formed between the amplified target region, if any, and the polynucleotide probe or probes.

In the above method, and as specific embodiments, the bacteria may be gram-positive or gram-negative or other defined bacterial species or group of species found in blood. Without being limited, the probe may be a universal bacterial probe, an *E. coli*/enteric probe, a gram-negative probe, a gram-positive probe, a Bacteroides probe, a probe for a species considered contaminant, or a combination of these probes.

The methods of the present invention thus enable determination of the presence of bacteria more rapidly than heretofore possible with prior art detection methods. The basic PCR process is carried out as follows.

A sample is provided which needs to be tested or is suspected of containing a particular nucleic acid sequence of interest, the "target sequence." The nucleic acid contained in the sample may be first reverse transcribed into cDNA (using Tth DNA polymerase as purified enzyme), if necessary, and then denatured, using any suitable denaturing method, including physical, chemical, or enzymatic means, which are known to those of skill in the art. A preferred physical means for strand separation involves heating the nucleic acid until it is completely (>99%) denatured. Typical heat denaturation involves temperatures ranging from about 80° C. to about 150° C., for times ranging from about 5 seconds to 10 minutes using current technology. Methods for the amplification of RNA targets using a thermostable DNA polymerase are described in PCT/US90/07641, filed Dec. 21, 1990, and incorporated herein by reference.

The denatured DNA strands are then incubated with the selected oligonucleotide palmers under hybridization conditions, conditions which enable the binding of the primers to the single oligonucleotide strands. As known in the art, the primers are selected so that their relative positions along a duplex sequence are such that an extension product synthesized from one primer, when it is separated from its complement, serves as a template for the extension of the other primer to yield a replicate chain of defined length.

The primer must be sufficiently long to prime the synthesis of extension products in the presence of the agent for polymerization. The exact length of the primers will depend on many factors, including temperature, source of the primer and use of the method. For example, depending on the complexity of the target sequence, the oligonucleotide primer typically contains about 15–30 nucleotides, although it may contain more or fewer nucleotides. Short primer molecules generally require cooler temperatures to form sufficiently stable hybrid complexes with the template. The primers must be sufficiently complementary to selectively hybridize with their respective strands.

The primers used herein are selected to be "substantially" complementary to the different strands of each specific sequence to be amplified. The primers need not reflect the exact sequence of the template, but must be sufficiently complementary to selectively hybridize with their respective strands. Non-complementary bases or longer sequences can be interspersed into the primer, or the primer can contain a subset complementary to the specific sequence provided that the primer retains sufficient complementarity with the sequence of one of the strands to be amplified to hybridize therewith, and to thereby form a duplex structure which can be extended by the polymerizing means. The non-complementary nucleotide sequences of the primers may include restriction enzyme sites. Appending a restriction enzyme site to the end(s) of the target sequence is particularly helpful for subsequent cloning of the target sequence.

Preferred oligonucleotide primers and probes for use in the present invention are shown in FIGS. 1–6. The oligonucleotide primers and probes may be prepared by any suitable method. For example, synthetic oligonucleotides can be prepared using the triester method of Matteucci et al., 1981, *J. Am. Chem. Soc.* 103:3185–3191. Alternatively automated synthesis may be preferred, for example, on a Biosearch 8700 DNA synthesizer using cyanoethyl phosphoramidite chemistry. Many methods for labeling nucleic acids, whether probe or primer, are known in the art and are suitable for purposes of the present invention. Suitable labels may provide signals detectable by fluorescence, radioactivity, colorimetry, X-ray diffraction or absorption, magnetism, enzymatic activity, and the like. Suitable labels include fluorophores, chromophores, radioactive isotopes (particularly $^{32}P$ and $^{125}I$), electrondense reagents, enzymes and ligands having specific binding partners. Enzymes are typically detected by their activity. For example, horseradish-peroxidase (HRP) can be detected by its ability to convert diaminobenzidine to a blue pigment. A preferred method for HRP based detection uses tetramethyl-benzidine (TMB) as described in *Clin. Chem.* 33:1368 (1987). An alternative detection system is the Enhanced Chemiluminescent (ECL) detection kit commercially available from Amersham. The kit is used in accordance with the manufacturer's directions.

Primers and probes are typically labeled with radioactive phosphorous $^{32}P$ by treating the oligonucleotides with polynucleotide kinase in the presence of radiolabeled ATP. However, for commercial purposes non-radioactive labeling systems may be preferred, such as, horseradish peroxidase-avidin-biotin or alkaline phosphatase detection systems. If the primer or one or more of the dNTPs utilized in a PCR amplification has been labeled (for instance, the biotinylated dUTP derivatives described by Lo et al., 1988, *Nuc. Acids Res.* 16:8719) instead of the probe, then hybridization can be detected by assay for the presence of labeled PCR product. Biotinylated primers can be prepared by direct biotinylation of the oligonucleotide. For 5' biotinylation of oligonucleotides during direct solid phase synthesis biotin-containing phosphoramidites were used according to Alves et al., 1989, *Tetra. Let* 30:3098; Cocuzza, 1989. *Tetra Let.* 30:6287; and Barabino et al., 1989, EMBO J. 8:4171. Solid phase synthesis of biotinylated oligonucleotides at any internal or terminal (5' or 3') position is also suitable for preparing biotinylated primers and probes (Pieles et al., 1989, NAR 18:4355, and Misiura et al., 1989, NAR 18:4345). Alternatively, primers can be biotinylated using terminal deoxynucleotide transferase (TdT) (Boeringer Mannheim).

Template-dependent extension of the oligonucleotide palmer(s) is then catalyzed by a polymerizing agent in the presence of adequate amounts of the four deoxyribonucleoside triphosphates (dATP, dGTP, dCTP, and dTTP) or analogs, in a reaction medium which is comprised of the appropriate salts, metal cations, and pH buffering system. Suitable polymerizing agents are enzymes known to catalyze primer-and template-dependent DNA synthesis. Known DNA polymerases include, for example, *E. Coli* DNA polymerase I or its Klenow fragment, T$_4$ DNA polymerase, Taq DNA polymerase and DNA polymerase from *Pyrococcus furiosus, Thermus thermophilus* (Tth), *Thermotoga maritima, Thermosipho africanus,* and *Thermococcus litoralis*. The reaction conditions for catalyzing DNA synthesis with these DNA polymerases are well known in the art.

The products of the synthesis are duplex molecules consisting of the template strands and the primer extension strands, which include the target sequence. These products, in turn, serve as templates for another round of replication. In the second round of replication, the primer extension strand of the first cycle is annealed with its complementary primer; synthesis yields a "short" product which is bounded on both the 5'-and the 3'-ends by primer sequences or their complements. Repeated cycles of denaturation, primer annealing, and extension result in the exponential accumulation of the target region defined by the primers. Sufficient cycles are run to achieve the desired amount of polynucleotide containing the target region of nucleic acid. The desired amount may vary, and is determined by the function which the product polynucleotide is to serve.

The PCR method can be performed in a number of temporal sequences. For example, it can be performed step-wise, where after each step new reagents are added, or in a fashion where all of the reagents are added simultaneously, or in a partial stepwise fashion, where fresh reagents are added after a given number of steps.

In a preferred method, the PCR reaction is carried out as an automated process which utilizes a thermostable enzyme. In this process the reaction mixture is cycled through a denaturing step, a primer annealing step, and a synthesis step. A DNA thermal cycler specifically adapted for use with a thermostable enzyme may be employed, which utilizes temperature cycling without a liquid-handling system, thereby eliminating the need to add the enzyme at every cycle. The types of machines are commercially available from Perkin-Elmer (Norwalk, CT): TC-1, TC-480, and TC-9600. The TC-9600 is most suitable for PCR assays being developed for commercial use.

After amplification by PCR, the target polynucleotides may be detected directly by gel analysis provided the target DNA is efficiently amplified and the primers are highly specific to the target region to be amplified. To assure PCR efficiency, glycerol and other related solvents such as dimethyl sulfoxide, can be used to increase the sensitivity of the PCR at the amplification level and to overcome problems pertaining to the sequencing of regions of DNA having strong secondary structure. These problems may include (1) low efficiency of the PCR, due to a high frequency of templates that are not fully extended by the polymerizing agent or (2) incomplete denaturation of the duplex DNA at high temperature, due to high GC content. The use of such solvents can increase the sensitivity of the assay at the level of amplification to approximately several femtograms of DNA (which is believed to correspond to a single bacterial cell). The concentration range for glycerol is about 5%–20% (v/v), and the DMSO concentration range is about 3%–10% (v/v).

Alternatively, the target polynucleotides may be detected by hybridization with a probe polynucleotide which forms a stable hybrid with the target sequence under high stringency to low stringency hybridization and wash conditions. If it is expected that the probes will be completely complementary (i.e., about 99% or greater) to the target sequence, stringent conditions will be used. If some mismatching is expected, for example if variant strains are expected with the result that the probe will not be completely complementary, the stringency of hybridization may be lessened. However, conditions are chosen which rule out nonspecific/adventitious binding. Conditions which affect hybridization and which select against nonspecific binding are known in the art (*Molecular Cloning A Laboratory Manual,* second edition, J. Sambrook, E. Fritsch, T. Maniatis, Cold Spring Harbor Laboratory Press, 1989). Generally, lower salt concentration and higher temperature increase the stringency of binding. For example, it is usually considered that stringent conditions are incubation in solutions which contain approximately 0.1×SSC, 0.1% SDS, at about 65° C. incubation/wash temperature, and moderately stringent conditions are incubation in solutions which contain approximately 1–2X SSC, 0.1% SDS and about 50%–65° C. incubation/wash temperature. Low stringency conditions are 2X SSC and about 30°–50° C.

An alternate method of hybridization and washing is to perform a low stringency hybridization (5×SSPE, 0.5% SDS) followed by a high stringency wash in the presence of 3M tetramethylammonium chloride (TMACl). The effect of the TMACl is to equalize the relative binding of A-T and G-C base pairs so that the efficiency of hybridization at a given temperature is a function of the length of the polynucleotide. Using TMACl, it is possible to vary the temperature of the wash to achieve the level of stringency desired.

Stringency requirements can be modified to alter target specificity as described. For example, where *Staphylococcus aureus* is to be detected, it is well within the scope of the invention for those of ordinary skill in the art to modify the stringency conditions described above and cause other Staphylococcus species to be excluded or included as targets. The novel 16S rRNA sequences provided herein are suitable for preparing a vast number of probe compounds having particular hybridization characteristics as desired.

Probes for bacterial target sequences may be derived from the 16S rRNA gene sequences or their complements. The probes may be of any suitable length which span the target region, but which exclude the primers, and which allow specific hybridization to the target region. As used herein "specific hybridization" refers to that hybridization pattern or character suitable for accurately identifying bacterial agents present in a sample. In a preferred embodiment, the invention is suitable for use as a panel array of probes. Consequently, the specific hybridization pattern for the panel is a composite of individual specific hybridization probes, which probes may individually include or exclude particular species, subtypes, or genera as desired. Thus, it may be preferable to prepare probes for specifically identifying each of *Staphylococcus aureus* and *S. epidermidis*. Alternatively, it may be suitable to prepare one probe for detecting any Staphylococcus species.

Generally, the probes will have at least 14 nucleotides, preferably at least 18 nucleotides, and more preferably at least 20 to 30 nucleotides of either of the complementary DNA strands. The target sequence can come from either complementary DNA strands. If there is to be complete complementarity, i.e., if the strain contains a sequence identical to that of the probe, since the duplex will be relatively stable under even stringent conditions, the probes may be short, i.e., in the range of about 10–30 base pairs. If some degree of mismatch is expected with the probe, i.e., if it is suspected that the probe will hybridize to a variant region, the probe may be of greater length, since length seems to counterbalance some of the effect of the mismatch (es).

The probe may be formed from a subset of the target region and therefore need not span the entire target region. Any subset of the target region can be used in constructing the probe provided the probe by hybridizing to that portion of the target region will specifically identify the target region. Consequently, the nucleic acid probe may be 10–40 nucleotides in length and hybridize to as few as 10 nucleotides of the target region. Further, fragments of the probes may be used so long as they are sufficiently characteristic of the bacterial species to be detected.

Analysis of the nucleotide sequence of the target region may be by direct analysis of the PCR amplified products as described in Gyllensten and Erlich, 1988, *Proc. Natl. Acad. Sci. USA* 85:7652, incorporated herein by reference.

It may be desirable to determine the length of the PCR product detected by the probe. This may be particularly true if it is suspected that variant bacterial strains may contain deletions or insertions within the target region, or if one wishes to confirm the length of the PCR product. In such circumstances, it is preferable to subject the products to size analysis as well as hybridization with the probe. Methods for determining the size of nucleic acids are known in the art, and include, for example, gel electrophoresis, sedimentation in gradients, and gel exclusion chromatography.

The presence of the target sequence in a biological sample is preferably detected by determining whether a hybrid has been formed between the probe and the nucleic acid subjected to the PCR amplification techniques. Methods to detect hybrids formed between a probe and a nucleic acid sequence are well-known in the art. For example, an unlabeled sample may be transferred to a solid matrix to which it binds, and the bound sample subjected to conditions which allow specific hybridization with a labeled probe; the solid matfix is then examined for the presence of the labeled probe.

Alternatively, if the sample is labeled, an unlabeled probe is bound to the matrix, and after exposure to the appropriate hybridization conditions, the matfix is examined for the presence of a label. Saiki et at., 1988, *Proc. Natl. Acad. Sci. USA* 86:6230, incorporated herein by reference, describe methods of immobilizing multiple probes on a solid support and using hybridization to detect the amplified target polynucleotides of interest. See also co-pending U.S. Ser. No. 07/414,542, filed Sep. 29, 1989, incorporated herein by reference. The latter two procedures are well suited to the use of a panel of probes which can provide different levels of identification of an amplified target DNA, depending on the type of information desired. In another alternative procedure, a solution phase sandwich assay may be used with labeled polynucleotide probes, and the methods for the preparation of such probes are described in U.S. Pat. No. 4,820,630, issued Apr. 11, 1989.

One approach to diagnosing bacterial septicemia is to run several different individual PCR assays. PCR detection of individual species of pathogenic bacteria causing meningitis has been described in the scientific literature. For example, Kuritza and Oehler, May, 1991, *Abstracts of the General Meeting of the ASM* page 84; Deneer and Boycjuk, 1991, *Applied and Environmental Microbiology* 57:606–609, and Kristiansen, 1991, *Lancet* 337:1568–1569.

Another approach, which is a preferred embodiment of the present invention, is to run a single PCR assay utilizing universal bacterial PCR primers and a panel of probes. Each probe is specific to a species or group of species which are commonly found in blood and will preferably be used simultaneously with other probes. The universal bacterial piers correspond to highly conserved regions of a gene found in most bacteria and hence are capable of amplifying the target gene of most bacterial species.

The degree of specificity desired for each probe is dictated by two major considerations (1) the probe should be broad enough in range to detect most of the strains of a given species which are found in clinical samples and (2) the probe should be narrow enough in range to exclude closely related species that are commonly found in blood. In some cases, a probe that is broad in range and detects some closely related species that are not found in blood is preferable to a narrower range probe that may not detect all the strains desired. Information on (1) the types of bacterial species found in blood and (2) species closely related to a given species are described in *Bergey's Manual of Systematic*

*Bacteriology* (ed. J. G. Holt, Williams and Wilkins, Baltimore, MD) and *The Manual of Clinical Microbiology* (ed. A. Balows, American Society for Microbiology, Washington, DC).

For the probes described, the prior art, while providing guidelines for the characteristics of optimal probes (such as the sequence in comparison to available nucleotide sequence data, a low degree of secondary structure and optimal length) does not provide a means of predicting the experimental performance of probes for detecting bacteria found in blood. This information must be discovered empirically by hybridization testing of many different isolates of the pathogens and of closely related species, as illustrated in the examples below. The nucleotide sequences, described as SEQ ID Nos. 1–25, provide preferred embodiments of the invention. However, providing the specific sequences and methods shown herein, one of ordinary skill in the art is enabled to prepare additional probes that are within the scope of the present invention.

Therefore, the probes described below are preferably applied to the detection of septicemia by using them in combination to detect and identify what bacteria are present in a blood sample. All of the probes described below, as well as additional probes, can be arranged in a reverse dot blot format, as described by Saiki et al. (supra.) Each of the probes is immobilized as a separate dot on a solid support such as a nylon membrane or microtiter plate. The amplified DNA is hybridized to each of the probes at the same time in an aqueous solution. The pattern of the signals from each of the dots (i.e., probes) indicates the identity of the target DNA. Accordingly, upon amplification of the target region (preferably by PCR), and application of the panel of probes described herein, hybridization of one or more of the probes in the panel (including the universal probe when applied to blood) will result in a positive signal and the positive identification of the bacterial species present as either *E. coli*/enteric bacteria, *Staphylococcus epidermidis*, *Propionibacterium acnes*, Propionibacterium species, Bacillus species, coagulase-negative Staphhylococci, Corynebacterium species, *Staphylococcus aureus*, or a bacterium which does not react with any of the more specific probes.

In one embodiment of the invention, the panel of probes includes a probe for detecting gram-positive bacteria, for example RW03 (5'-GACGTCAAATCATCATGCCCCTFATGTC-3'[SEQ ID No. 3]) and a probe for detecting gram-negative bacteria such as DL04 (5'-GACGTAAGGGCCATGATGACTIGACGTC-3'[SEQ ID No. 5]), RDR476 (5'-GACCTAAGGGCCATGATGACTYGACGTC-3'[SEQ ID No. 12]), RDR477 (5'-GACATAAGGGCCATGAGGACTTGACGTC-3'[SEQ ID No. 13]), or RDR278 (5'-GACGTAAGGGCCATGAGGACTTGACGTC-3'[SEQ ID No. 7]). However, because DL04 (SEQ ID No. 5) and RDR278 (SEQ ID No. 7) do not detect gram-positive Bacteroides, a separate probe, such as RDR279 (5'-GACGTAAGGGCCGTGCTGATTTGACGTC-3'[SEQ ID No. 11]) may be included. Suitable probes for specifically identifying these bacteria may be selected from but not limited to the preferred probes described as follows:

| *E. coli*/enteric bacteria | | |
|---|---|---|
| RDR140 | SEQ ID No. 10 | 5'-GGCGCTTACCACTTTGTGATTCATG-3' |
| *P. acnes* | | |
| RDR328 | SEQ ID No. 14 | 5'-GAGACCGGCTTTCCGAGATTCGCTC-3' |
| Propionibacterium species | | |
| COR44 | SEQ ID No. 15 | 5'-CCAACTTTCATGACTTGACGGG-3' |
| coagulase-negative Staphylococci and *Staphylococcus epidermidis* | | |
| COR02 | SEQ ID No. 16 | 5'-AGTAACCATTTGGAGCTAGCCGT-3' |
| COR05 | SEQ ID No. 17 | 5'-CGGCTAGCTCTAAAAGGTTACTCTA-3' |
| RDR512 | SEQ ID No. 18 | 5'-CGGCTAGCTCCAAAAGGTTACTCTA-3' |
| RDR325 | SEQ ID No. 19 | 5'-CGACGGCTAGCTCCAAATGGTTACT-3' |
| Corynebacterium species | | |
| COR36 | SEQ ID No. 20 | 5'-CACATGCTACAAGGGTCGGTACAGT-3' |
| RDR510 | SEQ ID No. 21 | 5'-ACTGTACCGACCATTGTAGCATGTG-3' |
| Bacillus species | | |
| RDR502 | SEQ ID No. 22 | 5'-GTATTCACCGCGGCATGCTGATCCG-3' |
| COR48 | SEQ ID No. 23 | 5'-TATTCACCGCGGCATGCTGAT-3' |
| *Staphylococcus aureus* | | |
| RDR327 | SEQ ID No. 24 | 5'-GCCGGTGGAGTAACCTTTTAGGAGC-3' |
| COR26 | SEQ ID No. 25 | 5'-CCGGTGGAGTAACCTTTTAGGA-3' |

Those skilled in the art will also be aware of the problems of contamination of a PCR by the amplified nucleic acid from previous reactions and non-specific amplification. Methods to reduce these problems are provided in PCT patent application Ser. No. 91/05210, filed Jul. 23, 1991, incorporated herein by reference. The method allows the enzymatic degradation of any amplified DNA from previous reactions and reduces non-specific amplification. The PCR amplification is carried out in the presence of dUTP instead of dTTP. The resulting double-stranded uracil-containing product is subject to degradation by uracil N-glycosylase (UNG), whereas normal thymine-containing DNA is not degraded by UNG. Adding UNG to the amplification reaction mixture before the amplification is started degrades all uracil-containing DNA that might serve as target. Because the only source of uracil-containing DNA is the amplified product of a previous reaction, this method effectively sterilizes the reaction mixture, eliminating the problem of contamination from previous reactions (carryover). UNG itself is rendered temporarily inactive by heat, so the denaturation steps in the amplification procedure also serve to inactivate the UNG. New amplification products, therefore, though incorporating uracil, are formed in an effectively .UN.G-free environment and are not degraded.

Also within the scope of the present invention are PCR kits for use in carrying out any of the aforementioned PCR processes. The diagnostic kits include the probe polynucleotide(s) and the primers in separate containers. Either of these may or may not be labeled. If unlabeled, the ingredients for labeling may also be included in the kit. The kit may also contain other suitably packaged reagents and material needed for the particular hybridization protocol, for example, standards, and/or polymerizing agents, as will as instruction for conducting the test.

In use, the components of the PCR kit, when applied to a nucleic acid sample, create a reagent mixture which enables the detection and amplification of the target nucleic acid sequence. The reagent mixture thus includes the components of the kit as well as a nucleic acid sample which contains the polynucleotide chain of interest. The teachings of the references cited in the present application are incorporated herein by reference.

A variation of this invention is to use an alternate method of producing the amplified target region. For example, the TAS amplification system, (Kwoh et al., 1989, *Proc. Natl. Acad. Sci. USA* 86:1173–1177) and its modification, SSSR (Guatelli et al., 1990, *Proc. Natl. Acad. Sci. USA* 87:1874–1878) is a method for amplifying RNA or DNA templates using cycles consisting of a cDNA step to produce a cDNA copy of an RNA template, and an RNA transcription step to increase the copy number of the eDNA or DNA template. This method, like PCR, employs two oligonucleotide primers which hybridize to opposite strands of the target region and flank the target region. The universal bacterial primers described herein may, with minor modifications (the addition of RNA polymerase promoter sequences at the 5'end of one of the primers), be used in a TAS or SSSR amplification system. The subsequent step of the assay, detection by the oligonucleotide probes described herein, may be carried out essentially as described above for the PCR-based assay or may be done using a bead-based sandwich hybridization system (Kwoh et al.).

The nucleotide sequence data described herein can also provide specific detection of bacterial species when used in other nucleic acid-based assays. For example, the nucleotide sequence information discovered for *S. pneumoniae* and *S. Agalactiae* indicated that there is a single base-pair mismatch between these two organisms in the region of the *S. pneumoniae* probe RDR224 (SEQ ID NO. 23). This mismatch could be used in a ligase chain reaction system to provide discrimination between these two organisms in a clinical sample (Wu and Wallace, 1988, *Genomics* 4:560–569). The ligase chain reaction involves the use of two sets of oligonucleotide primers. Each primer within the set is complementary to the other. The different sets of primers are located directly adjacent to each other along the template. A single base pair mismatch in between the two sets of primers disrupts the reaction, whereas a perfect match between the primer sets and the template results in target amplification. In another example, the sequence of probes described herein could be used to design corresponding probes in a signal amplification system such as the Q beta replicase system (Kramer and Lizardi, 1989, *Nature* 339:401–402, and Lomeli et al., 1989, *Clin. Chem.* 35:1826–1831 ). This system involves an RNA probe containing the specific probe sequence inserted into the MDV-1 variant of the Q-beta RNA genome. The RNA probe is replicated using Q-beta replicase, producing up to $10^{12}$ molecules per reaction, after hybridization of the probe to the sample to be assayed.

By way of further specificity, the following probe and primer nucleotide base pair data is provided:

Probe RDR245 (5'-GTACAAGGCCCGGGAACGTATTCACCG-3'[SEQ ID No. 9]) corresponds to the complement of nucleotide base numbers 1369–1395 in the *E. coli*. 16S ribosomal RNA gene as specified in reference of Neefs et al.

Primer RW01 (5'-AACTGGAGGAAGGTGGGGAT-3' [SEQ ID No. 2]) corresponds to nucleotide base numbers 1170–1189 in the *E. Coli* 16S ribosomal RNA gene as specified in Neefs reference.

Primer DG74 (5'-AGGAGGTGATCCAACCGCA-3' [SEQ ID No. 1]) corresponds to the complement of nucleotide base numbers 1522–1540 in the *E. Coli* 16S ribosomal RNA gene as specified in Neefs reference.

Probe RW03 (5'-GACGTCAAATCATCATGCCCCTTATGTC-3'[SEQ ID No. 3]) corresponds to nucleotide base number 1190–1217 in the *E. coli* 16S ribosomal RNA gene as specified in Neefs reference.

Probes DL04 (SEQ ID No. 5) and RDR278 (5'-GACGTAAGGGCCATGAGGACTTGACGTC-3'[SEQ ID No. 7]) corresponds to the complement of nucleotide base number 1190–1217 in the *E. Coli* 16S ribosomal RNA gene as specified in Neefs reference.

Probe RDR140 (SEQ ID No. 10) corresponds to nucleotide base number 1458–1482 in the *E. Coli* 16S ribosomal RNA gene as specified in Neefs reference.

Probe RDR279 (SEQ ID No. 11) corresponds to the complement of nucleotide base number 1190–1217 in the *E. Coli* 16S ribosomal RNA gene as specified in Neefs reference.

Oligonucleotide probes based on the 16S rRNA gene for the detection of nucleic acids from various microorganisms have been described in the scientific literature. For example, universal bacterial probes have been described by Wilson et at., 1990, *J. Clinical Microbiology* 28:1942–1946, and Chem et al., 1989, *FEMS Microbiology Letters* 57:19–24. Examples of genus- and species-specific probes have been described by Barry et al., 1990, *Biotechnology* 8:233–236, Atlas and Bej, "*PCR protocols: A guide to method and application,*" p. 399–406; and in Genprobe international patent application W088/03957 (these references are incorporated herein by reference). The invention claimed in this application differs from these inventions in the range of bacteria detected. The gram-positive and gram-negative probes detect a range of different bacterial genera and are therefore more specific than universal bacterial probes and more broad than genus- or species-specific probes. Using a panel including a universal bacterial probe, gram-positive and gram-negative probes and species or group specific probes, it is possible to obtain a more reliable detection of a bacterium than the use of a collection of genus- or species-specific probes, since it is possible for the universal bacterial and gram-negative or gram-positive probes to detect bacteria which are not detected by any of the more specific probes. The panel described also provides more clinically useful information than a single universal bacterial probe; since different antibiotic therapy is recommended for gram-negative versus gram-positive bacterial infections.

The following examples are intended to be illustrative of the various methods and compounds of the invention.

EXAMPLE 1

Probe Design

The candidate Gram-negative probes RW04 (5'-GACGTCAAGTCATCATGGCCCTTACGTC-3'[SEQ ID No. 4]), DL04 (SEQ ID No. 5), DL05 (5'-GTAAGGGCCATGATGACTTGAC-3'[SEQ ID No. 6]), and RDR278 (SEQ ID No. 7), the gram-positive probe RW03 (SEQ ID No. 3), and the Bacteroides probe RDR279 (SEQ ID No. 11) were designed from data in the Genbank or EMBL nucleotide sequence libraries (Dams et al., 1990, Nucleic Acids Research, Vol. 16, Supplement and Neefs, et al., "Compilation of small ribosomal subunit RNA sequences", Vol. 18, Supplement, 1990) and in Woese, 1987, Microbiological Reviews 51(2):221–271, which references are incorporated herein by reference.

The location of the probes was chosen based on the finding of regions in the 16S rRNA gene which contain "sequence signatures" unique to the various groups of bacteria (Woese Supra.). All six probes are located in the same region of the gene. The nucleotide sequence of the probes was designed based on the sequences available for each group of bacteria to be detected and compared to corresponding sequences in groups of bacteria that were to be excluded. For example, the Gram-positive probe was designed to match most of the sequences found in most Gram-positive bacteria and to differ from the corresponding sequences in Gram-negative bacteria.

The candidate universal bacterial probes RDR244 (5'-CGGTGAATACGTYCCCGGGCCTYGTAC-3'[SEQ ID No. 8]) and RDR245 (SEQ ID No. 9) correspond to a highly conserved region of the 16S rRNA gene. Most of the probe sequence in this region is present in most of the bacterial species for which sequence information is available and is not present in the nuclear or mitochondrial DNA of eukaryotic species.

In addition, each of the oligonucleotides described above was examined for self complementarity (ability to form base pairs with itself) using a computer program called FOLD in the University of Wisconsin series of programs. The position of the oligonucleotide probe was chosen to minimize the formation of secondary structure where it was possible to do so while still maintaining the desired specificity. The position of the oligonucleotide probe was chosen to minimize the formation of secondary structure where it was possible to do so while still maintaining the desired specificity (delta G>-3.0 kcal).

The E. coli/enteric bacteria probe was designed from data in Gertbank. The probe was designed using the following steps:

First, the nucleotide sequence from bp 1430 to 1536 (as specified Neefs supra.) within the 370 bp region bounded by amplification primers RW01 (SEQ ID No. 2) and DG74 (SEQ ID No. 1) for E. coli and Proteus vulgaris was compared to that of a panel of nonenteric species, including Neisseria gonorrhoeae, Pseudomonas aeruginosa, and Pseudomonas testosteroni. Regions where differences in the sequence occurred were noted and used to design a candidate probe.

Second, the candidate probe was compared with the corresponding nucleotide sequence of more phylogenetically diverse species listed in Genbank or EMBL to ensure that the candidate oligonucleotide would not detect other species. Third, the oligonucleotide was examined for self complementarity using a computer program called OLIGO, (National Biosciences, Hamel, MN). The position of the oligonucleotide probe was chosen to minimize the formation of secondary structure where it was possible to do so while still maintaining the desired specificity.

EXAMPLE 2

Specificity Testing of Probe DL04 (SEQ ID NO. 5)

For specificity testing of DL04, PCR amplification of gram-negative or gram-positive bacterial DNA was accomplished as follows. The primers utilized were DG74 (SEQ ID No. 1) and RW01 (SEQ ID NO. 2).

A standard PCR 2×mix was made containing the following for amplifying a target sequence for both gram-positive and gram-negative bacteria:

10×standard PCR buffer 10.0 ml 50 mM $MgCl_2$ 1.0 ml dNTP's (2.5 mM total dNTP's) 2.5 ml palmer RW01 (SEQ ID No. 2) (50 mM) 1.0 ml primer DG74 (SEQ ID No. 1) (50 mM) 1.0 ml $H_2O$ Taq DNA polymerase (5 U/ml) 0.5 ml The 10×standard PCR buffer contains:

100 mM Tris-HCl, pH8.3

500 mM KCl 15 mM MgCl

DNAs were prepared by SDS-proteinase K lysis followed by phenol:chloroform extraction. Bacterial strains were obtained from the ATCC.

A. Fifty µl of a gram-negative or gram-positive bacterial DNA sample was mixed together with 50 µl of the PCR 2×mix.

The reaction mixture was placed in a 0.5 ml microfuge tube and the tube was placed in a thermal cycler manufactured by Perkin-Elmer. A two-step PCR cycle was used and the thermocycler was set as follows:

1. Time delay file—5 minutes at 95° C.
2. Thermocycle file—95° C. for 25 seconds 55° C. for 25 seconds, each incubation for 25 to 35 cycles.
3. Time delay file—10 minutes at 72° C.

B. Detection of amplified products

After the amplification reaction is complete, 5 ml of the 100 µl PCR reaction was mixed with 1 µl of 10×DNA dye buffer (50% sucrose, 10 mM Tris, pH 7.5, 1 mM EDTA, 1.0% SDS, 0.05% bromphenol blue). The sample was loaded onto a 2% Nusieve agarose, 0.5% Seakern agarose, 1×TBE (45 mM Tris-borate, 1 mM EDTA) gel. After running the bromphenol blue dye front to the bottom of the gel, the gel was stained with ethidium bromide (5 µg/ml), washed in water and photographed under UV light using a Polaroid camera and an orange filter.

The size of the PCR product is approximately 370 bp.

C. Transfer of amplified DNA to nylon membrane

After photography of the gel, the gel was soaked in 0.25 N HCl for 10 minutes at room temperature. The gel was rinsed in water and then soaked in solution of 0.5N NaOH, 1.5M NaCl for 30 minutes. The gel was then rinsed in water and then soaked in a solution of 1 M Tris, pH 7.5, 1.5 M NaCl for 30 minutes.

DNA was then transferred to a nylon membrane (Pall Biodyne) presoaked in water by one of two ways: (1) vacuum transfer using a Stratagene Stratavac vacuum blotter or (2) capillary transfer by the method of Southern.

After transfer, DNA was fixed to the membrane using UV light in a Stratagene Stratalinker.

D. Radioactive labeling of oligonucleotide probe DL04 (SEQ ID No. 5).

Oligonucleotide DL04 was labeled using $T_4$ polynucleotide kinase in the following reaction mix:

q-32-P ATP 10 µl

10×kinase buffer 2.5 µl oligonucleotide (10 µM) 2.0 µl $H_2O$ 8.5 µl $T_4$ polynucleotide kinase 2.0 µl 10×kinase buffer contains:

500 mM Tris, pH 8

100 mM MgCl$_2$ 50 mM DTT

The kinase reaction mixture was incubated for 30 minutes at 37° C. 5.6 of 0.25 M EDTA and 169.4 ml of H$_2$O were added to stop the reaction. This mixture was loaded onto a 1.0 ml capacity column of Biogel P4 and spun in a tabletop centrifuge for 5 minutes at 5,000 rpm to separate the labeled oligonucleotide from the unincorporated radioactivity. 1 ml of the eluate from the column was counted in a scintillation counter without added scintillation fluid (Cerenkov counting) to obtain an estimate of the level of incorporation of radioactivity. A volume giving approximately 1×10$^6$ cpm was used for each blot in the subsequent hybridization.

E. Hybridization of probes with DNA

The DNA blots were prehybridized in a mixture of 5×SSPE, 0.5% SDS at 60° C. (1X SSPE=0.18 M NaCl, 10 mM NaPO$_4$, pH 7.4, 1 mM EDTA). The labeled oligonucleotide probe was added to 7.5 ml of 5×SSPE, 0.5% SDS and mixed. The solution was added to the plastic bag containing the presoaked blot. The blot was incubated for 1 to 18 hours at 60° C.

The blot was removed from the plastic bag and placed in a solution of 2×SSPE, 0.1% SDS and washed for 10 minutes at room temperature. The blot was then washed in a solution of 3M tetramethylammonium chloride (TMACl), 50 mM Tris, pH8 and 0.2% SDS for 10 minutes at 64° C. for gram-negative probe DL04 (SEQ ID No. 5).

The blot was air-dried and wrapped in Saran wrap and placed in a X-ray film holder with a sheet of Kodak XAR-5 X-ray film with or without an intensifying screen for 1 to 72 hours at −70° C.

EXAMPLE 3

Specificity Testing of Probe RW03 (SEQ ID No. 3)

Probe RW03 (SEQ ID No. 3) was tested against gram-positive and gram-negative bacteria using the same methods and materials as Example 2 except as follows:

Fifty μl of a gram-positive or gram-negative containing DNA sample was added to the PCR 2×mix.

The probe used was the gram-positive specific probe RW03 (SEQ ID No. 3). In step E, when the blot was washed in a solution of 3M TMACl, 50 mM Tris, pH8 and 0.2% SDS, it was done at 62° C. instead of 64° C. as was done for the gram-negative test.

EXAMPLE 4

Comparison of Probes RW04 (SEQ ID No. 4) and DL04 (SEQ ID No. 5)

Candidate Gram-negative probe RW04 (SEQ ID No. 4) was labeled with $^{32}$P and hybridized to PCR products from various bacterial DNA's as described of Gram-negative probe DL04 (SEQ ID No. 5) in Example 2, except that the wash in TMACl was done at 62° C. The results of the hybridizations are shown in FIG. 1 and summarized in FIG. 3. The top panel of FIG. 1 shows a Southern blot hybridized with DL04 (SEQ ID No. 5); the bottom panel shows a Southern blot hybridized with RW04 (SEQ ID No. 4). The data show that the hybridization results obtained by the two probes are different even though both probes were designed to be Gram-negative "universal" probes. RW04 (SEQ ID No. 4) gave a positive signal for many Gram-positive species it should not have detected; while DL04 (SEQ ID No. 5) gave positive signals for only the Gram-negative species it should have detected (with the exception of *T. martima* and *T. thermophilus*, which are not human pathogens). DL04 SEQ ID No. 5) was therefore selected as a probe useful for detecting Gram-negative bacteria. Further testing (FIG. 4) indicated that DL04 (SEQ ID No. 5) did not detect all gram-negative species. A second candidate gram-negative probe, RDR278 (SEQ ID No. 7), was tested as follows in Example 5.

EXAMPLE 5

Specificity Testing of RDR278 (SEQ ID No. 7)

Probe RDR278 (SEQ ID No. 7) was tested using the same methods and materials as Example 2 including the wash in TMACl which was done at 64° C.

Gram-negative probe RDR278 (SEQ ID No. 7) was labeled with $^{32}$P and hybridized to PCR products from various bacterial DNA's. The data are presented in FIG. 4. RDR278 (SEQ ID No. 7) gave a positive hybridization signal for most of the species not detected by DL04 (SEQ ID No. 5). The exception among the species tested was *Bacteroides, fragilis*, for which a separate probe was designed. Therefore, it is observed that the combination of Gram-negative probes DL04 (SEQ ID No. 5) and RDR278 (SEQ ID No. 7) detect the majority of Gram-negative bacteria tested.

EXAMPLE 6

Specificity Testing of "Universal" Bacterial

Probes RDR244 (SEQ ID No. 8) and RDR245 (SEQ ID No. 9)

The methods and materials of Example 2 were used including the wash in TMACl, which was done at 64° C.

Candidate Universal bacterial probes RDR244 (SEQ ID No. 8) and RDR245 (SEQ ID No. 9), corresponding to a highly conserved region in the 16S rRNA gene, were labeled with $^{32}$P and hybridized to PCR products from various bacterial DNA's. In FIG. 2, panels A (lanes 1–28 and 29–45) show a Southern blot hybridized with RDR244 (SEQ ID No. 8). Panels B (lanes 1–28 and 29–45) show a Southern blot hybridized with RDR245 (SEQ ID No. 9). The probes performed differently even though both probes were designed to detect any bacterial species. It is observed that, among the bacterial species tested, RDR244 (SEQ ID No. 8) detected all but two species: *Peptostreptococcus magnus* and *P. anaerobius*. RDR245 (SEQ ID No. 9) detected all of the bacterial species tested. Therefore, RDR245 (SEQ ID No. 9) was selected as the universal bacterial probe.

EXAMPLE 7

Specificity Testing of Probe RDR279 (SEQ ID No. 11)

The methods and materials of Example 2 were used including the wash in TMACl, which was done at 64° C.

Probe RDR279 (SEQ ID No. 11), corresponding to a region which is a sequence signature for Bacteroides, ref.), was labeled with $^{32}$P and hybridized to PCR products from various bacterial DNA's. FIG. 4 summarizes the results of testing of RDR279 (SEQ ID No. 11) against other bacterial species. The probe detected *Bacteroides fragilis* and did not give a reaction with any of the other bacterial species tested.

The probes described above are applied to the detection of septicemia by using them in combination to detect and identify what bacterium is present in a blood sample. All of the probes described above, as well as additional probes, can be arranged in a reverse dot blot format, as described by Saiki et al. The probes are immobilized on a solid support such as nylon membrane or microliter plate. The amplified DNA is hybridized to each of the probes at the same time in an aqueous solution. The pattern of the signals from each of the probes indicates the identity of the target DNA. For example, if the DNA is from a gram-negative bacterium, the amplified will only react with the universal bacterial probe and one of the gram-negative probes. If the DNA is from a gram-positive species, it will give a positive reaction only with the universal bacterial probe and the gram-positive probe. If the DNA is from a Bacteroides species, it will give a positive signal with the universal bacterial probe and the Bacteroides probe. If the DNA is from a bacterium which is neither gram-negative nor gram-positive (such as *T. pallidum*, a spirochete) it will react only with the universal bacterial probe. If there is no bacterial DNA present, none of the probes will give a positive signal.

Although the foregoing invention has been described in some detail for the purpose of illustration, it will be obvious that changes and modifications may be practiced within the scope of the appended claims by those of ordinary skill in the art.

EXAMPLE 8

Preparation of Low-DNA Taq Polymerase

To increase sensitivity of the present methods, it may be desirable to use amplification cycle numbers higher than 25 (e.g., 26–40). However, the extreme sensitivity of such a reaction using the universal primers disclosed may lead to artifactual results due to amplification of residual DNA in commercial reagents. For high cycle number the following procedure eliminates DNA contamination in the agent for polymerization.

Equipment Required

Biorad Econo-pac Q cartridge; Biorad catalog #732–0021

Sterile disposable 50 mL polypropylene tubes; Corning catalog #25330–50

HPLC/FPLC flow adaptors; Biorad Catalog #732–0111/ 732–0112.

General laboratory equipment

Peristaltic pump (flow rate 0.5–2 mL capability)

Reagents Required

Formulation buffer: 20 mM Tris, 0.1M KCl, 0.5% NP40, 5% Tween-20, 1 mM DTT, 0.1 mM EDTA, 50% glycerol, pH 8

Econo-pac Q wash buffer: 200 mM Tris/1 M KCl, pH 8.8

0.5N Acetic acid 1.0N Sodium hydroxide

Sterile Glass distilled water

10% bleach

70% Ethanol

Procedure

A. Preparation of laminar flow hood, peristaltic pump, and cartridge fittings

1. Wipe down the hood with 10% bleach.
2. Install the peristaltic pump with tubing and cartridge HPLC/FPLC flow adaptors.
3. Install the column support stand and clamps into the hood.
4. Turn on UV lamp for 30 minute to irradiate surfaces.
5. Rinse pump tubing with 20 mL 70% Ethanol at a flow rate of 1 mL/min.
6. Rinse tubing with 50 mL sterile glass distilled water at a flow rate of 1 mL/min.
7. Discard the wash fluid.

B. Washing the Econo-pac Q cartridge

Note: All washes are to be performed using the peristaltic pump at a flow rate not exceeding 2 mL/min. Discard all wash fluid after use. All operations carded out in the hood.

1. Attach cartridge to the column support stand.
2. Connect tubing to the cartridge by the flow adaptors.
3. Wash cartridge with 20 mL sterile GD water.
4. Wash cartridge with 50 mL 0.5N acetic acid.
5. Wash cartridge with 50 mL 1.0N sodium hydroxide.
6. Wash cartridge with 50 mL Econo-pac Q wash buffer.
7. Wash cartridge with 50 mL Formulation buffer.
8. Calibrate flow rate to 0.5 mL/min.

C. Loading and Collecting AmpliTaq® DNA Polymerase

1. Remove AmpliTaq®DNA polymerase stock from −20° C. freezer. Allow to thaw at room temperature for 30 minutes.
2. In the hood, add 100 mL of AmpliTaq®DNA polymerase to a sterile, heat treated 250 mL flask.
3. Replace the stock AmpliTaq®DNA polymerase into the freezer.
4. Load AmpliTaq®onto the cartridge at a flow rate of 0.5 mL/min.
5. Collect 5 mL into a tube, then switch to a clean 50 mL tube. Discard the 5 mL aliquot.
6. Collect 25 mL aliquots of AmpliTaq®DNA polymerase into sterile 50 mL tubes.

EXAMPLE 9

A Preferred Method for Analysis of Clinical Samples

Two modifications of the amplification conditions in Example 2 are preferred when testing clinical samples. First, modifications which greatly reduce the possibility of carry-over contamination are used. The nucleotide dUTP is substituted for TTP in the amplification mix, and uracil-N-glycosylase (Perkin Elmer) is added to the amplification mix. Under the appropriate conditions of concentration and incubation, these modifications degrade any U-containing PCR product that may contaminate the reaction.

The second modification is to treat the amplification reagents to reduce the level of contaminating bacterial DNA present. This allows amplification cycle numbers higher than 25 to be used for increased sensitivity. The 10X Taq buffer (11210 mM Tris-HCl, pH 8.3, 500 mM KCl) is autoclaved and sterilely dispensed. Eight mM $MgCl_2$ is autoclaved and sterilely dispensed. Water is ultrafiltered and autoclaved. TE buffer (10 mM Tris-HCl, 0.1 mM EDTA, pH 8.0) is autoclaver.

The solution of dNTPs (dATP, dGTP, dCTP, dUTP) is filtered through a Centricon-30 filter (Amicon catalog number 4208). The C-30 filtrate cup and cap are autoclaved and the filter unit is soaked in 10% bleach for 1 hour. The filters are thoroughly rinsed in autoclaved ultrafiltered water. The filters are then spun with 400 µl of autoclaved ultrafiltered water. The dNTP solution is centrifuged through the treated C-30 filter units once for 30 minutes at 5000×g in a fixed angle rotor.

The primers at 200 uM concentration are filtered through Millipore M-100 PTHK filters (catalog number UFC3THYK00). The Eppendorf tube part of the filter unit is autoclaved and the filtrate cup is soaked in 10% bleach for 1 hour. The filters are thoroughly rinsed in autoclaver ultrafiltered water. The filters are then spun with 400 μl of autoclaved ultrafiltered water at 5000×G for 3 minutes in an Eppendorf microfuge. Each primer is successively filtered 4 times, each time through a clean filter for 3 minutes at 5000μg. The primers are diluted 1:250 for a $OD_{260}$ reading. Primer concentration is adjusted using autoclaved TE buffer to 20 um.

The 4×PCR mix is made up as follows:
  400 μl 10X Taq buffer
  40 μl 100 mM dNTP mix or 400 μl of a mixture of equal volumes of 10 mM of each dNTP
  80 μl of 20 uM RW01 (SEQ ID No. 2)
  80 μl of 20 uM DG74 (SEQ ID No. 1)
  20 μl of low-DNA Taq polymerase (5 units/μl)
  380 μl of ultrafiltered water The amplification mix is made up as follows (in order):
  25 μl 4×PCR mix
  25 μl mM $MgCl_2$
  2 drops mineral oil (Sigma #M5904)
  50 μl of DNA sample The amplification conditions in the thermal cycler TC-480 (Perkin Elmer) are:
  50° C., 2 minutes (optional)
  95° C., 1 minute (optional)
  Cycling:
  95° C., 30 seconds
  72° C., 20 seconds
  55° C., 30 seconds for 30 to 35 cycles 72° C., 7 minutes to overnight Detection is performed as described in Example 4.

Although the foregoing invention has been described in some detail for the purpose of illustration, it will be obvious that changes and modifications may be practiced within the scope of the appended claims by those of ordinary skill in the art.

We claim:

1. A method for determining the presence of a gram negative bacterial polynucleotide in a sample suspected of containing said gram negative bacterial polynucleotide, wherein said bacterial polynucleotide comprises a selected target region, said method comprising:

(a) amplifying the target region, if any, to a detectable level;

(b) incubating the amplified target region, if any, with a polynucleotide probe consisting of a nucleotide sequence selected from the group consisting of
5'-GACGTAAGGGCCATGATGACTTGACGTC-3' (SEQ ID No. 5), the sequence complementary to SEQ ID No.5,
5'-GACGTAAGGGCCATGAGGACTTGACGTC-3' (SEQ ID No. 7), and the sequence complementary to SEQ ID No. 7, under conditions which allow hybridization of the probe to the amplified target region; and (c) detecting hybrids formed between the amplified target region, if any, and the polynucleotide probe.

2. The method of claim 1, wherein the target sequence is amplified by means of PCR.

3. A composition for detecting gram negative bacterial species comprising a polynucleotide hybridization assay probe consisting of the sequence
5'-GACGTAAGGGCCATGATGACTTGACGTC-3' (SEQ ID No. 5), or its complementary sequence.

4. A composition for detecting gram negative bacterial species comprising a polynucleotide hybridization assay probe consisting of the sequence
5'-GACGTAAGGGCCATGAGGACTTGACGTC-3' (SEQ ID No. 7), or its complementary sequence.

5. A PCR kit for the detection of gram negative bacterial species comprising a pair of polynucleotide probes, wherein a first probe consists of the sequence
5'-GACGTAAGGGCCATGATGACTTGACGTC-3' (SEQ ID No. 5) or a sequence complementary thereto, and a second probe consists of the sequence 5'-GACGTAAGGGCCATGAGGACTTGACGTC-3' (SEQ ID No. 7) or a sequence complementary thereto.

* * * * *